United States Patent [19]

Andra

[11] 4,039,775
[45] Aug. 2, 1977

[54] UNIFORM TEMPERATURE INCUBATOR

[75] Inventor: John R. Andra, Pittsburgh, Pa.

[73] Assignee: Fisher Scientific Company, Pittsburgh, Pa.

[21] Appl. No.: 618,498

[22] Filed: Oct. 1, 1975

[51] Int. Cl.² .............................................. F27D 11/02
[52] U.S. Cl. ..................................... 219/385; 219/406; 219/407; 219/522; 219/543
[58] Field of Search ............... 219/203, 385, 386, 397, 219/406, 407, 521, 522, 543; 126/200

[56] References Cited

U.S. PATENT DOCUMENTS

| 3,263,063 | 7/1966 | Marriott et al. | 219/522 |
| 3,299,253 | 1/1967 | Lawson, Jr. | 219/385 |
| 3,336,465 | 8/1967 | Hurko | 219/397 |
| 3,376,405 | 4/1968 | Gowor | 219/385 |
| 3,524,920 | 8/1970 | Stromquist et al. | 219/543 X |
| 3,553,426 | 1/1971 | Fink | 219/406 |
| 3,712,268 | 1/1973 | Reed | 219/385 X |
| 3,876,859 | 4/1975 | Franz et al. | 219/385 |
| 3,878,361 | 4/1975 | Levin et al. | 219/522 |
| 3,918,783 | 11/1975 | DuRocher et al. | 219/522 X |
| 3,928,748 | 12/1975 | Sauer | 219/522 |

Primary Examiner—Volodymyr Y. Mayewsky
Attorney, Agent, or Firm—Webb, Burden, Robinson & Webb

[57] ABSTRACT

An improved incubator includes a heated door which increases temperature uniformity inside the incubator.

10 Claims, 5 Drawing Figures

1

UNIFORM TEMPERATURE INCUBATOR

FIELD OF THE INVENTION

This invention relates to an improved incubator, especially for laboratory use, and particularly to an incubator door which provides a marked increase in temperature uniformity inside the incubator.

BACKGROUND OF THE INVENTION

Laboratory incubators are generally constructed in a rectangular box-like configuration. The chamber of the incubator may have a water jacket, a so-called "wet" incubator, in which water is heated to maintain the inside of the incubator at a substantially constant, predetermined temperature such as 37° C (body temperature). Dry incubators are also used. Both types of incubators have at least one door which forms one side of the incubator chamber and provides access to the interior of the incubator chamber. In some incubators there are two doors, the outer door being metal and the inner door containing a light, such as a pane of glass, for viewing specimens in the incubator chamber without disturbing the thermal equilibrium of the incubator environment. In those incubators in which there is only one door, it may include the light.

Heretofore, incubator doors, although an integral part of the chamber construction, have not included any satisfactory means for heating the incubator chamber. Consequently, all of the heat required has been provided by radiant type, open-coil heaters in the dry incubators or by thermal transfer from the water jacket through the remaining five sides (the three vertical sides, the top and the bottom) of the wet incubators, or by use of an open-coil heater in the outer doors of some incubators. None of these designs has achieved the high level of uniformity in incubator temperature which the present invention has achieved through the use of a heated door and particularly a heated glass light in an incubator door.

Although heated lights have been used in other applications, e.g. as automobile window defrosters, the particular heated glass light door construction herein disclosed is not known nor has any heated glass door been used in an incubator for laboratory use.

SUMMARY OF THE INVENTION

To obtain substantial temperature uniformity in a laboratory incubator, five sides of the incubator chamber are heated by thermal transfer from an open-coil heater or through a conventional water jacket or the like and the sixth side is heated by improved means comprising a heated glass light in either the inner or outer incubator door. The light includes a heating element comprising an electrical circuit or a ceramic grid having at least a pair of electrical bus bars which extend along opposite edges of the light. The bus bars are connected to an appropriate power source, preferably 12 volts stepped down from 120 v. A.C., 60 Hz. A plurality of spaced electrical conductors are connected between the bus bars in substantially parallel relationship to each other across the entire surface of the light. Preferably, the heating element is printed upon the inside of the light by known techniques, such as silk screening. In a preferred embodiment there are two bus bars along a top edge of the light, each connected to one half of the conductors employed. The operation of the heating element is automatically controlled by a comparator which compares the temperature of the heated light with a desired preset temperature. Since the comparator is also electrically connected to means for measuring the temperature of the water in the water jacket surrounding the chamber in a "wet incubator" or to means for measuring the average temperature of the environment in a dry incubator, the comparator provides a command signal to activate or deactivate the heating element in accordance with the incubator temperature desired. Further and other features and advantages of the invention will become apparent from the following description of the invention.

DESCRIPTION OF THE PREFERRED EMBODIMENT OF THE INVENTION

Figure 1:
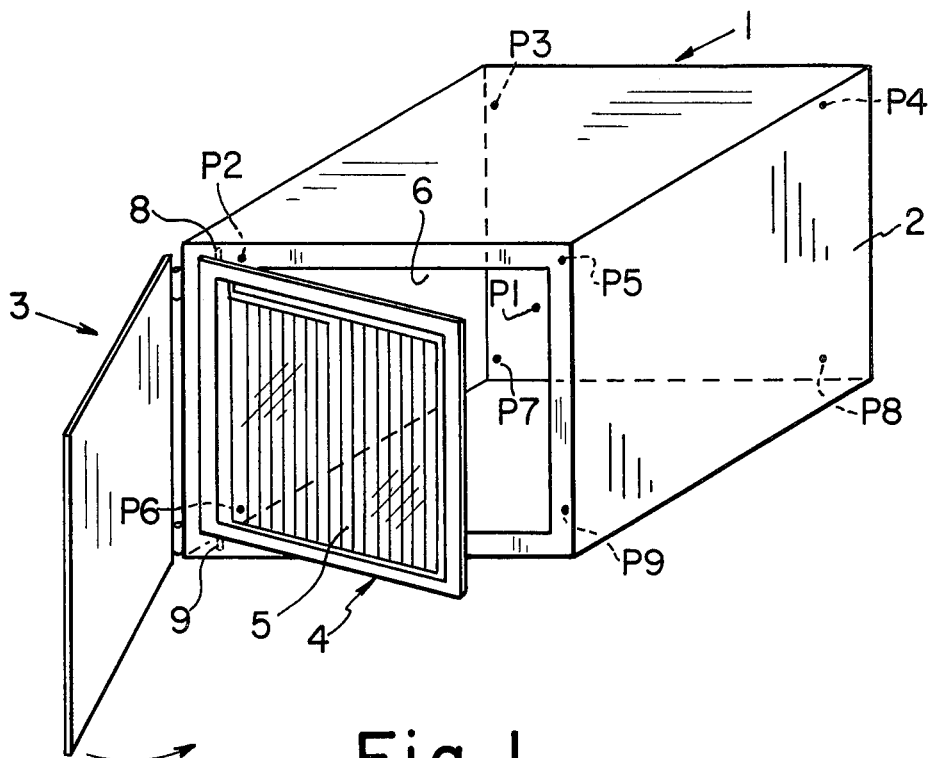
FIG. 1 is a perspective view of an incubator including an inner door having a heated glass light.

An incubator (FIG. 1) comprises a housing 1 which has a rectangular box-like configuration of five sides 2 (including the top and bottom) and an outer metal door 3. Each side is heated by means of an open-coil heater or by a thermal transfer from water in a water jacket adjacent each such side. An inner door 4 includes a glass light 5 through which the interior of the incubator chamber 6 can be observed.

Figure 2:
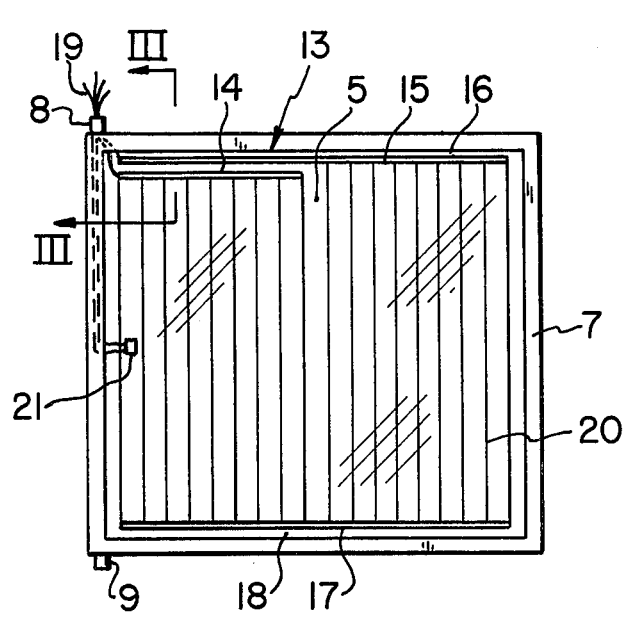
FIG. 2 is an elevational front view of the incubator door in accordance with the invention.
Figure 3:
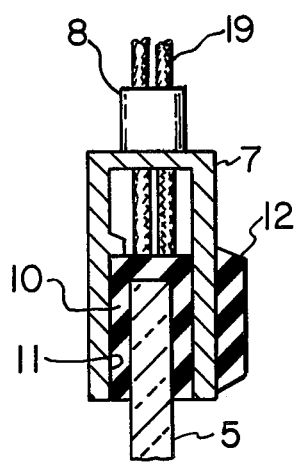
FIG. 3 is an enlarged cross-sectional view of a part of the incubator door taken along lines III—III of FIG. 2.

According to the present invention, the glass light 5 is electrically heated (FIGS. 2 and 3) and forms a part of the inner door 4, which provides substantially improved temperature uniformity within the incubator chamber. The light 5 is mounted in a frame 7 of extruded aluminum, pivotally mounted to the housing by hinges 8, 9. The light comprises a pane of glass, preferably double strength, type B, heavy duty glass manufactured, for example, by PPG Industries, Pittsburgh, Pensylvania. It is mounted in a C-shaped extruded rubber gasket 10 located in channel-shaped opening 11 in the frame 7. A gasket 12 is also provided for sealing the door when it is closed against the front edges of the walls 2 of the housing.

An electrical heating element or grid 13 is printed on the inside of the glass pane or light 5 (as installed in an incubator), by one of the known techniques, such as silk screening. The grid includes at least two bus bars, one along each opposite edge of the pane. It is preferred to use a pair of bus bars 14, 15 at the top edge 16 and a single bus bar 17 along the lower edge 18. The bus bars are connected through leads 19, which preferably extend through hollow hinges 8, to an appropriate power source (not shown).

A plurality of spaced electrical conductors 20 extend from bus bars 14, 15 to bus bar 17, with one half of the conductors being connected to bar 14 and the balance to bus bar 15. Current is circulated from bus bar 14 through one half of the conductors 20 to bar 17 and thence from bar 17 through the other conductors to bar 15.

Figure 4:
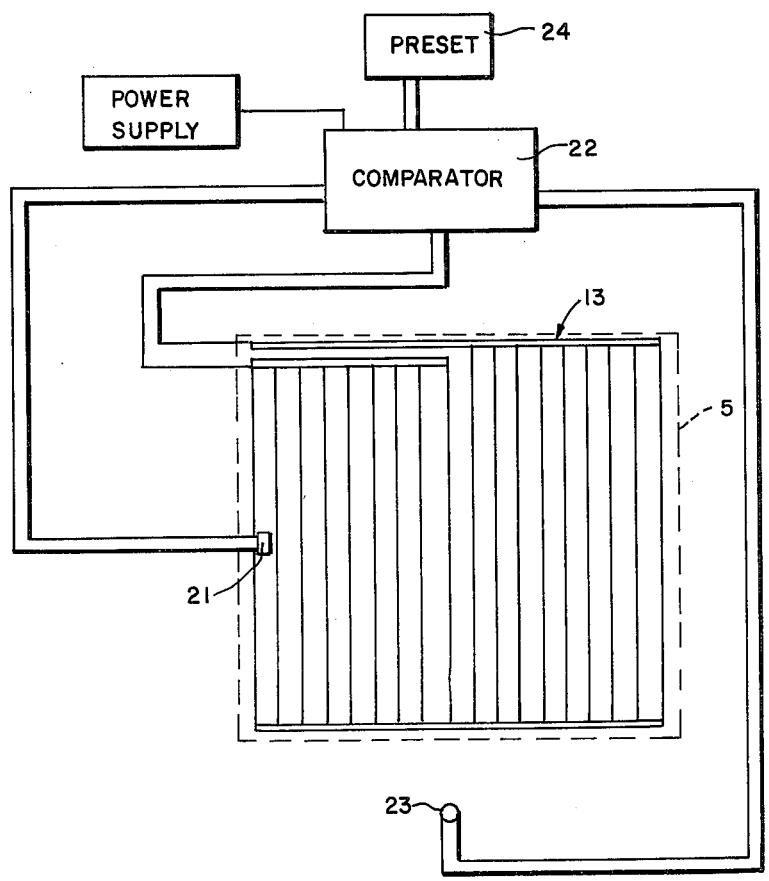
FIG. 4 is a schematic view of a comparison circuit for a wet incubator.

The grid 13 is controlled automatically to provide the appropriate amount of heat to maintain the incubator chamber at the desired or preset temperature. The grid control system comprises a comparison circuit (FIGS. 4 and 5) which includes a comparator 22 to which the grid 13 on glass light 5 is electrically connected. It also includes a temperature probe, such as thermistor 21 which is bonded to the inside of the light. In the case of a "wet" incubator (schematically shown in FIG. 4), the comparator 22 is also electrically connected to a temperature sensing probe 23 which extends into the bottom of the water jacket surrounding the chamber. Since the temperature of the water in the entire water jacket is substantially uniform, the temperature measured by the temperature sensing probe 23 is indicative of the temperature of the chamber. By comparing the temperature signal corresponding to the water temperature with a preset signal 24 corresponding to the desired temperature and the temperature signal from thermistor 21 corresponding to the temperature of the heated light with the preset signal, the comparator 22 can provide a command signal to electrically activate or deactivate the grid 13 in accordance with the incubator temperature desired.

Figure 5:
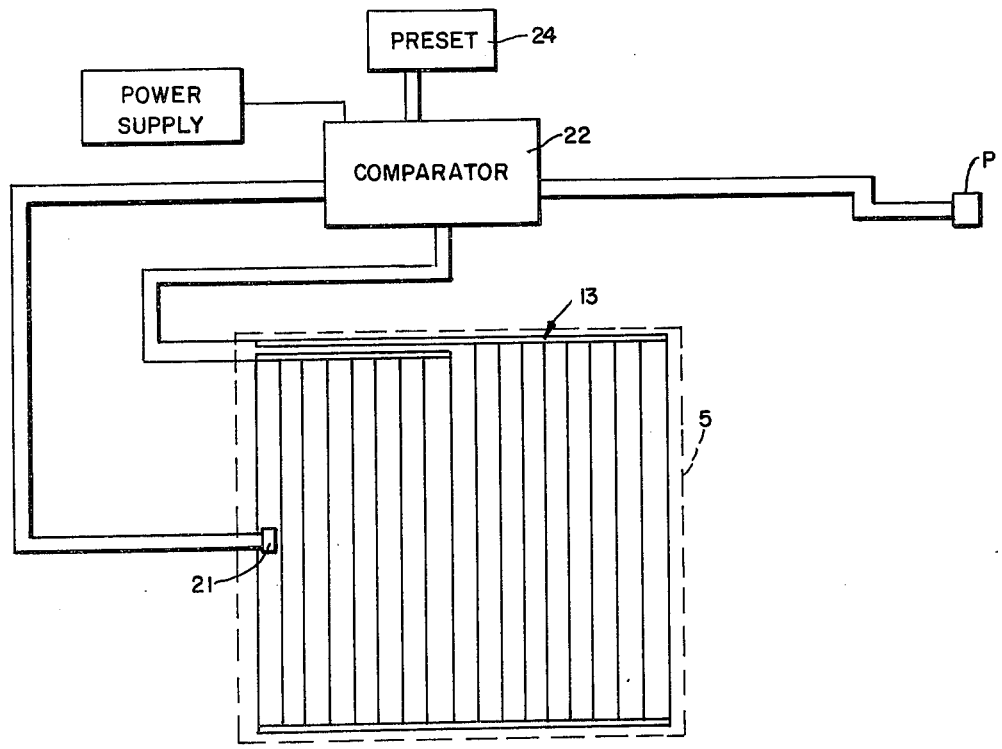
FIG. 5 is a schematic view of a comparison circuit for a "dry" incubator.

The electrical connection of the grid 13 on glass light 5 and the thermistor 21 to the comparator 22 is the same in a dry incubator (schematically shown in FIG. 5). However, in a dry incubator the comparator 22 is electrically connected to a temperature sensing probe P which extends, preferably, through the rear side of the incubator and into approximately the geometric center ($P_1$) of the incubator chamber (See FIG. 1). Thus, the comparator receives a signal 24 from the thermistor and compares it with a preset temperature signal and also receives a temperature signal from the probe P near $P_1$ and compares it with the preset signal 24. The comparator provides a command signal to the grid 13 to electrically activate or deactivate the grid in accordance with the incubator temperature desired. The form of the comparator for use in either the wet or dry incubator may be any of those which are well known to those of ordinary skill in the art. It must be responsive to the preset temperature signal corresponding to the incubator temperature desired, and a signal corresponding to the temperature of the incubator chamber, and a signal corresponding to the temperature of the light.

To demonstrate improved uniformity of temperature, a pane of 0.125 thick double strength B grade glass, clear and fully tempered, was used in a test chamber (incubator). Printed on the inside of the glass was an 18-parallel 0.025 wide ceramic grid or silver frit heating element connected in series by 0.310 wide ceramic silver bus bars. The silver frit was applied to the glass by a silk screen process.

The test chamber had a rectangular housing. Thermocouples were located at nine points, in accordance with applicable ASTM procedure, corresponding to each corner and the geometric center of the chamber. Measuring point extremities were located two inches from the enclosure walls. These nine points are indicated as $P_1, P_2 \ldots P_9$ in FIG. 1.

The environment in the test chamber was composed of air and 0-20% $CO_2$ by volume with water vapor maintained at over 90% relative humidity.

The chamber 6 was heated to a temperature of 37° C by an open coil heater controlled to maintain approximately that temperature. The average temperature of the chamber was measured by a resistance temperature detector (RTD) meter located in the control panel of the incubator and coupled to a thermistor probe located within the chamber adjacent its geometric center (i.e., $P_1$).

Temperature measurements were made at the appropriate nine points using thermocouples. These point temperature measurements were averaged. The average measurement was then compared with each of the point temperature measurements.

The average deviation was then determined by averaging the temperature deviations between the average temperature measurement and each of the point temperature measurements.

It was found that without a heated glass light in the door sealing the test chamber opening the following average deviations from the average temperature prevailed:

| Temp. Readout Front Panel Meter (° C) | $CO_2$ Tension (%) | Average Deviation (° C) |
|---|---|---|
| 37.9 | 10 | .520 |
| 37.9 | 10 | .450 |
| 37.1 | 15 | .482 |
| 37.0 | 20 | .420 |
| 37.0 | 20 | .500 |

The heated glass light door was then used to seal the test chamber opening. The average deviations from the average temperature were determined:

| Temp. Readout Front Panel Meter (° C) | $CO_2$ Tension (%) | Average Deviation (° C) |
|---|---|---|
| 37.0 | 0 | .385 |
| 37.0 | 10 | .334 |
| 37.0 | 20 | .349 |

From the foregoing test data, it will be observed that the average temperature deviation is decreased by approximately 0.12° C using the heated glass light door. This is a significant decrease of slightly more than 30%. Consequently, with the heated glass light door, a specimen, regardless of its location in the incubator, is assured of subtantially more uniform temperature across it and in its relationship with other specimens in the incubator chamber.

The heated glass light may be used, as described herein, in the inner door of an incubator. Where the incubator has only a single door, the heated glass light may form a part thereof. Of course, more or less than 18 conductors may be employed depending upon the size of the glass light required to close the door opening and the amount of heat to be radiated from the glass light into the chamber. Similarly, the grid spacing may be changed and/or it may be printed on the outside of the glass. In addition, the light may be formed from two panes of glass between which is sandwiched an appropriate nonconductive substrate, such as a plastic, upon which is applied a heating element comprising an electrical circuit or grid in accordance with the present invention. The thickness of the glass may also be increased or decreased depending upon the desired temperature gradiant across the glass and the amount of heat required by the incubator chamber.

Having described a presently preferred embodiment of the invention, it is to be understood that it may be otherwise embodied within the scope of the appended claims.

I claim:

1. An incubator having substantial temperature uniformity comprising:
   A. a housing having a plurality of walls defining an incubator chamber and having an opening for obtaining access to the chamber;
   B. heating means for heating the chamber;
   C. a door for sealing the opening in the housing;
   D. a glass light in the door for observing the interior of the chamber; and
   E. an electric heating element applied to a surface of the glass light, the heating element comprising at least one pair of bus bars, one located along each opposite edge of the glass light and having a plurality of conductors connected between the bus bars, the conductors being substantially parallel to each other and spaced over substantially the entire area of the glass.

2. An incubator as set forth in claim 1 wherein the heating element is applied to a surface thereof by printing.

3. An incubator as set forth in claim 1, the light comprising a pane of double strength, heavy duty glass which is clear and fully tempered.

4. An incubator as set forth in claim 1 in which the heating element comprises a sliver frit.

5. An incubator as set forth in claim 1 in which there are two bus bars along one edge of the glass light and a third bus bar along an opposite edge of the light, one of the two bus bars being substantially one half the length of the other and the other bus bar being substantially the length of the third bus bar, one half of the conductors being connected to each of the first mentioned bus bars and all of the conductors being connected to the third bus bar such that there is a series electrical connection between the first mentioned bus bars and the ends of the first mentioned bus bars are closely adjacent one another.

6. An incubator as set forth in claim 1 wherein the light is mounted in an extruded frame hingedly secured to the housing.

7. An incubator as set forth in claim 1 in which the heated door is the inner door of two doors.

8. An incubator as set forth in claim 1 wherein the heating element is automatically controlled by a comparator which is responsive to a preset temperature signal corresponding to the incubator temperature desired, a signal corresponding to the temperature of the incubator chamber, and a signal corresponding to the temperature of the light, the comparator being a part of a comparison circuit comprising:
   A. a preset unit for providing a preset temperature signal and connector to the comparator;
   B. a temperature sensing probe for sensing the temperature of the incubator chamber and connected to the comparator;
   C. A temperature probe for sensing the temperature of the light and connected to the comparator; and
   D. the bus bars of the heating element being electrically connected to the comparator, whereby the heating element is controlled to maintain uniformity of temperature within the chamber.

9. An incubator as set forth in claim 1 wherein the light comprises two panes of glass and the heating element is applied to a substrate sandwiched between the panes.

10. An incubator as set forth in claim 1, the heated door comprising an extruded metal rectangular frame member including a C-shaped channel, a C-shaped insulation gasket in the channel, and the glass light being positioned in the C-shaped insulation gasket.

* * * * *